(12) United States Patent
Cheal (10) Patent No.: US 8,101,413 B2
(45) Date of Patent: Jan. 24, 2012

(54) AUTO-CALIBRATION CIRCUIT FOR ANALYTE MEASUREMENT

(75) Inventor: Stephen P. Cheal, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 258 days.

(21) Appl. No.: 12/503,659

(22) Filed: Jul. 15, 2009

(65) Prior Publication Data

US 2011/0011151 A1    Jan. 20, 2011

(51) Int. Cl.
*G01N 37/00* (2006.01)

(52) U.S. Cl. ......... 436/8; 436/149; 436/150; 422/82.01; 73/1.01; 73/1.02

(58) Field of Classification Search ............... 436/8, 14, 436/63, 149, 150; 422/82.01; 73/1.01, 1.02, 73/1.03; 204/403.01, 403.03
See application file for complete search history.

(56) References Cited

U.S. PATENT DOCUMENTS

| | | | |
|---|---|---|---|
| 4,929,426 A | 5/1990 | Bodai et al. | |
| 4,940,945 A | 7/1990 | Littlejohn et al. | |
| 5,379,214 A | 1/1995 | Arbuckle et al. | |
| 5,580,794 A | 12/1996 | Allen | |
| 5,728,352 A | 3/1998 | Poto et al. | |
| 5,795,543 A | 8/1998 | Poto et al. | |
| 5,837,546 A | 11/1998 | Allen et al. | |
| 5,856,195 A | 1/1999 | Charlton et al. | |
| 6,377,894 B1 | 4/2002 | Deweese et al. | |
| 6,600,997 B2 | 7/2003 | Deweese et al. | |
| 6,773,671 B1 | 8/2004 | Lewis et al. | |
| 7,041,206 B2 | 5/2006 | Gephart et al. | |
| 7,316,929 B2* | 1/2008 | Purcell | 436/8 |
| 7,875,240 B2* | 1/2011 | Perry et al. | 422/64 |
| 7,918,121 B2* | 4/2011 | Schell | 73/1.02 |
| 7,919,045 B2* | 4/2011 | Perry et al. | 422/64 |
| 2001/0023324 A1 | 9/2001 | Pronovost et al. | |
| 2002/0059030 A1 | 5/2002 | Otworth et al. | |
| 2002/0133080 A1 | 9/2002 | Apruzzese et al. | |
| 2004/0012676 A1 | 1/2004 | Weiner et al. | |
| 2005/0057676 A1 | 3/2005 | Weiner et al. | |
| 2005/0142033 A1 | 6/2005 | Glezer et al. | |
| 2006/0042964 A1 | 3/2006 | Mansouri et al. | |
| 2006/0108218 A1 | 5/2006 | Gephart et al. | |
| 2006/0189895 A1 | 8/2006 | Neel et al. | |
| 2009/0214384 A1* | 8/2009 | Wang et al. | 422/56 |
| 2009/0301166 A1* | 12/2009 | Charlton et al. | 73/1.02 |

* cited by examiner

*Primary Examiner* — Maureen Wallenhorst
(74) *Attorney, Agent, or Firm* — Nixon Peabody LLP (57) ABSTRACT

Embodiments provide expanded ability to communicate calibration information to diagnostic systems for determining a characteristic of a test sample. An example system for determining a characteristic of a test sample includes: a test sensor for receiving a test sample; a sensor meter responsive to the test sensor, the sensor meter determining a characteristic of the test sample received on the test sensor; and a calibration element including electrical contacts readable by the sensor meter. The electrical contacts are configurable in one of a plurality of patterns that communicates, to the sensor meter, information relating to the determination of the characteristic of the test sample. The plurality of patterns include two or more of the electrical contacts that are electrically isolated from any other electrical contacts. The sensor meter determines at least partially the information from the electrical contacts by determining a combination of values corresponding to the isolated electrical contacts.

32 Claims, 6 Drawing Sheets

AUTO-CALIBRATION CIRCUIT FOR ANALYTE MEASUREMENT

BACKGROUND OF THE INVENTION

1. Field of the Invention

The present invention generally relates to auto-calibration for analyte measurement by a meter, and, more particularly, to an auto-calibration circuit, such as an auto-calibration label, that provides extended read and decode functionality for a meter.

2. Description of Related Art

The field of clinical chemistry is concerned with the detection and quantization of various substances in body material, typically body fluids such as blood, urine or saliva. In one important aspect of this field, the concentration of naturally occurring substances, such as cholesterol or glucose, in an individual's blood is determined. One of the most frequently used analytical devices in clinical chemistry for determining the concentration of an analyte in a fluid sample is the test sensor. When the test sensor receives the fluid sample, certain reagents incorporated into the sensor react with the analyte in the fluid sample and provides a detectable signal, which indicates the concentration of the analyte. The signal may be a change in color as in the case of a colorimetric sensor or a change in current or potential as in the case of an electrochemical system. Those systems which employ an enzyme in the reagent system may be referred to as biosensors since they rely on the interaction of the enzyme (a biological material) with the analyte to provide the detectable response. This response, whether it be a change in color or in current or in potential, is typically measured by a meter, into which the sensor is inserted. The meter then displays a readout of the corresponding analyte concentration on a graphical user interface.

In particular, the determination of glucose in blood is of great importance to diabetic individuals who must frequently check the level of glucose to regulate their diets and their medications. While the remainder of the disclosure herein may be directed towards the determination of glucose in blood, it is to be understood that the procedure and apparatus of this invention can be used for the determination of other analytes in other body fluids or even non-fluid body materials such as the detection of occult blood in fecal material upon selection of the appropriate enzyme. In addition such sensors can be used in, for example, testing for meat spoilage or foreign substances in well water.

Diagnostic systems, such as blood glucose meters, typically calculate the actual analyte concentration according to a measured output and the known reactivity of the reagent on the test sensor. The reactivity of the reagent, however, may depend on manufacturing variations between lots of test sensors. To account for these variations and ensure proper calculation of the analyte concentration, the diagnostic systems may require some calibration. Various techniques have been used to communicate calibration information to diagnostic systems. The calibration information, for example, may include a code of characters and/or numbers that the diagnostic system translates, via a stored lookup table, into calibration coefficients that are used with equations to calculate the analyte concentration. In some systems, the user of the system may receive and manually enter calibration information into the system. In other systems, a calibration element, which may be similar to a test sensor, may provide readable calibration information when inserted into the system. In yet other systems, a memory element may be connected directly to a processor of the system to provide readable calibration information.

SUMMARY OF THE INVENTION

In view of the foregoing, embodiments according to aspects of the present invention provide systems and methods for communicating calibration information to diagnostic systems for more accurately determining a characteristic of a test sample. In particular, the embodiments provide expanded ability to communicate calibration information. In addition, the embodiments provide the ability to organize sets of calibration codes into a plurality of types that are efficiently read and decoded.

According to one example embodiment, a system for determining a characteristic of a test sample includes: a test sensor for receiving a test sample; a sensor meter responsive to the test sensor, the sensor meter determining a characteristic of the test sample received on the test sensor; and a calibration element including electrical contacts readable by the sensor meter. The electrical contacts are configurable in one of a plurality of patterns that communicates, to the sensor meter, information relating to the determination of the characteristic of the test sample. The plurality of patterns include two or more of the electrical contacts that are electrically isolated from any other electrical contacts. The sensor meter determines at least partially the information from the electrical contacts by determining a combination of values corresponding to the isolated electrical contacts.

In further embodiments, the test sensor includes a reagent that reacts with the test sample, the sensor meter determines the characteristic of the test sample by measuring the reaction between the reagent and the test sample, and the measurement by the sensor meter is calibrated by the information from the calibration element. For example, the information from the calibration element relates to a source for the reagent on the test sensor, and the information calibrates the sensor meter to account for the source.

In other embodiments, the plurality of patterns for the electrical contacts represents binary values, and the sensor meter determines at least partially the information from the electrical contacts by determining a combination of binary values corresponding to the isolated electrical contacts.

In additional embodiments, the values associated with the isolated electrical contacts are unique.

In further embodiments, the plurality of patterns are organized into types, and the combination of values corresponding to the isolated electrical contacts indicates one of the types. For example, the sensor meter is one of a plurality of sensor meter types, the plurality of patterns are operable with the plurality of sensor meter types and are organized into the sensor meter types, and the combination of values corresponding to the isolated electrical contacts indicate a type corresponding to the sensor meter.

In other embodiments, the sensor meter determines the information from the calibration element and translates the information into coefficients for an equation that determines the characteristic of the test sample.

In additional embodiments, the plurality of patterns for the electrical contacts includes at least one subset of the electrical contacts being electrically connected to each other, and the sensor meter further determines the information from the electrical contacts by determining a value corresponding to the at least one subset of connected electrical contacts. For example, the plurality of patterns for the electrical contacts includes a first subset of the electrical contacts connected to each other via a first conductive path and a second subset of the electrical contacts connected to each other via a second conductive path. In a further example, the sum of the value corresponding to the first subset of connected electrical contacts and the value corresponding to the second subset of connected electrical contacts uniquely corresponds to the combination of values corresponding to the isolated electrical contacts.

In further embodiments, a sensor package is receivable by the sensor meter, and the sensor package contains the test sensor and including the calibration element.

In other embodiments, the test sample is a fluid sample and the characteristic is a concentration of an analyte in the fluid sample.

Correspondingly, a method for determining a characteristic of a test sample, includes: receiving a test sample; reading an calibration element, the calibration element including electrical contacts configurable in one of a plurality of patterns to communicate information relating to a determination of a characteristic of the test sample, the plurality of patterns including two or more of the electrical contacts being electrically isolated from other electrical contacts; determining at least partially the information from the electrical contacts by determining a combination of values corresponding to the isolated electrical contacts; and determining a characteristic of the test sample according to the information from the calibration element.

According to yet other embodiments, a system for providing a calibration circuit with a type indicator includes: an electrical circuit; and a calibration circuit including electrical contacts readable by the electrical circuit. The electrical contacts are configurable in one of a plurality of patterns that communicates, to the electrical circuit, information relating to the determination of the characteristic of the test sample. The plurality of patterns include two or more of the electrical contacts being electrically isolated from any other electrical contacts. The electrical circuit determines at least partially the information from the electrical contacts by determining a combination of values corresponding to the isolated electrical contacts. The plurality of patterns are organized into types, and the combination of values corresponding to the isolated electrical contacts indicates one of the types for the calibration circuit.

These and other aspects of the present invention will become more apparent from the following detailed description of the preferred embodiments of the present invention when viewed in conjunction with the accompanying drawings.

DETAILED DESCRIPTION

Figure 1A:
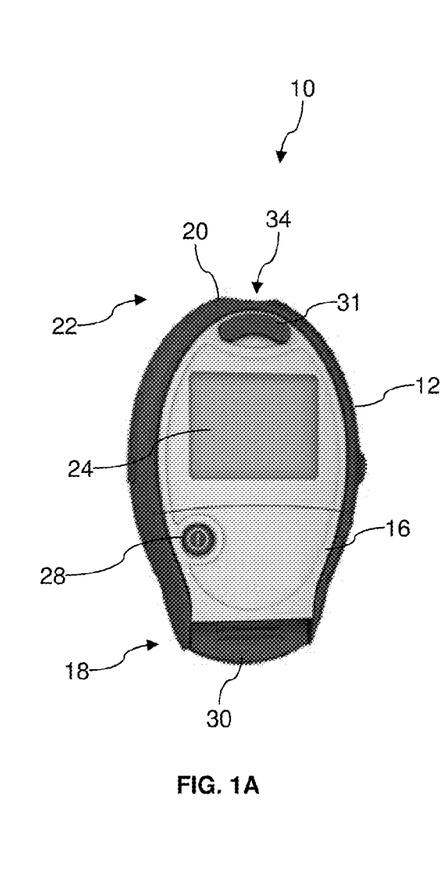
FIG. 1A illustrates an example sensor meter that may be employed according to aspects of the present invention.
Figure 1B:
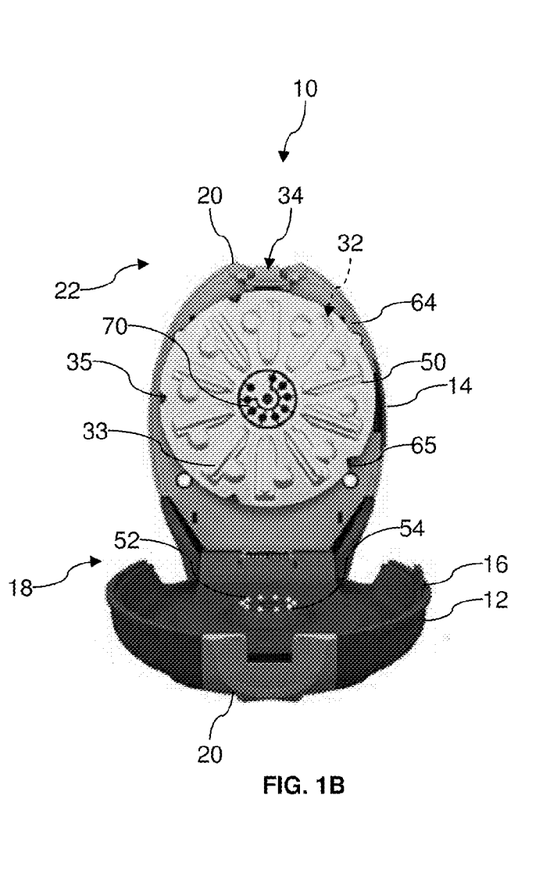
FIG. 1B illustrates the example sensor meter of FIG. 1A receiving a sensor package according to aspects of the present invention.

Referring to FIGS. 1A-B, a sensor meter 10 operable according to aspects of the present invention is illustrated. In particular, the sensor meter 10 includes a clam-shell type housing enclosure 12 formed by a base member 14 and a cover member 16. The base and cover members 14 and 16 are pivotably attached together at a first end 18 and are secured together by a locking device 20 at a second, opposite end 22. A display 24, such as a liquid crystal display (LCD), is disposed on the cover member 16. A power button 28 is alternately pressed to turn the sensor meter 10 on and off. Other buttons, switches, controls, and similar user interface mechanisms (not shown) may also be provided for inputting data and commands and for controlling the operation of the sensor meter 10. Such buttons, switches, and controls may be employed, for example, to select predefined operational modes for the sensor meter 10, to set, recall, and delete blood glucose readings, or to set the date, time, and other options. The sensor meter 10 includes a push/pull mechanism 30 at the first end 18. Manual engagement of the push/pull mechanism 30 by a user of the sensor meter 10 causes a test sensor 32 to be moved partially through a slot 34 into a position to receive a fluid sample, such as a blood sample, outside the enclosure 12. In addition, the sensor meter 10 includes a release button 31 that releases the test sensor 32 from the slot 34 for disposal after use. Although FIGS. 1A-B illustrate the sensor meter 10 with a particular configuration, it is understood that other sensor meters may be employed in accordance with aspects of the present invention.

FIG. 1B further illustrates a sensor package 50 containing a plurality of test sensors 32 used in combination with the sensor meter 10. Sensor meter cover member 16 supports an auto-calibration plate 52 and a predetermined number of auto-calibration pins 54. For example, FIG. 1B shows ten auto-calibration pins 54. The auto-calibration pins 54 are connected to associated sensor circuitry (not shown) located in the sensor meter 10. An indexing disk 64 is provided within the base member 14. The indexing disk 64 includes locking projections 65 for engagement with cooperative triangular shaped recessed portions 35 of the sensor package 50 for receiving and retaining the sensor package 50 on the indexing disk 64.

The sensor meter 50 calculates test values, such as blood glucose concentration, associated with the fluid sample according to a measured output and the known reactivity of a reagent on the test sensor 32. The reactivity of the reagent, however, may depend on manufacturing variations between lots of test sensors 32. To account for these variations and ensure correct calculation of the test values, the sensor meter 50 requires calibration. In particular, the sensor meter 10 calculates the test values by solving an equation, and coefficients for the equation may be varied to account for variations in the reagent between lots. As shown in FIG. 1B, calibration codes are encoded on an auto-calibration circuit 70 disposed on the sensor package 50. In some embodiments, the calibration codes may be encoded on a circuit on a substrate that forms a part of the sensor package 50. In other embodiments, the calibration codes may be encoded on a label that is formed on a separate substrate which is affixed to the sensor package 50. When a label is employed, an auto-calibration circuit may be conventionally referred to as "an auto-calibration label." In general, the term "auto-calibration circuit" as used herein refers to an element that provides calibration codes regardless of how it is made or formed. When the sensor package 50 is received by the sensor meter 10, associated electronic circuitry in the sensor meter 10 automatically reads and decodes the auto-calibration circuit 70 before a sensor 32 is used. The sensor meter 10 determines the equation coefficients from the calibration code provided by the corresponding auto-calibration circuit 70. For example, an algorithm may be employed to calculate the equation coefficients from the calibration code or a stored lookup table may be employed to translate the calibration code into the equation coefficients. The auto-calibration circuit 70 can be implemented according to digital, mechanical, analog, or optical techniques, or any combination thereof.

Figure 7:
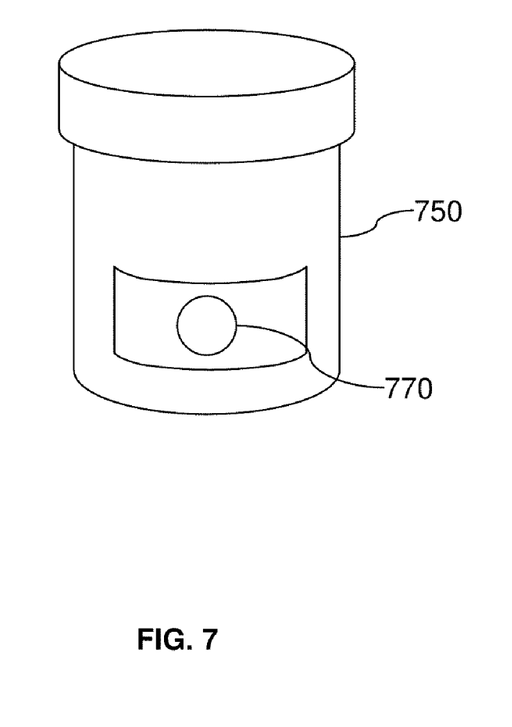
FIG. 7 illustrates an example container that includes an auto-calibration circuit according to aspects of the present invention.

Although FIG. 1B illustrates an auto-calibration circuit 70 on a disk-shaped sensor package 50, it is understood that an auto-calibration circuit according to aspects of the present invention may be implemented on devices having other configurations. For example, as illustrated in FIG. 7, an auto-calibration circuit 770 is provided on the exterior surface of a cylindrical container 750 containing test sensors for use with a sensor meter. In this example, the container 750 can be positioned relative to a sensor meter so that the auto-calibration circuit 770 can be read by the sensor meter to obtain calibration codes corresponding to the test sensors in the container 750.

Figure 2:
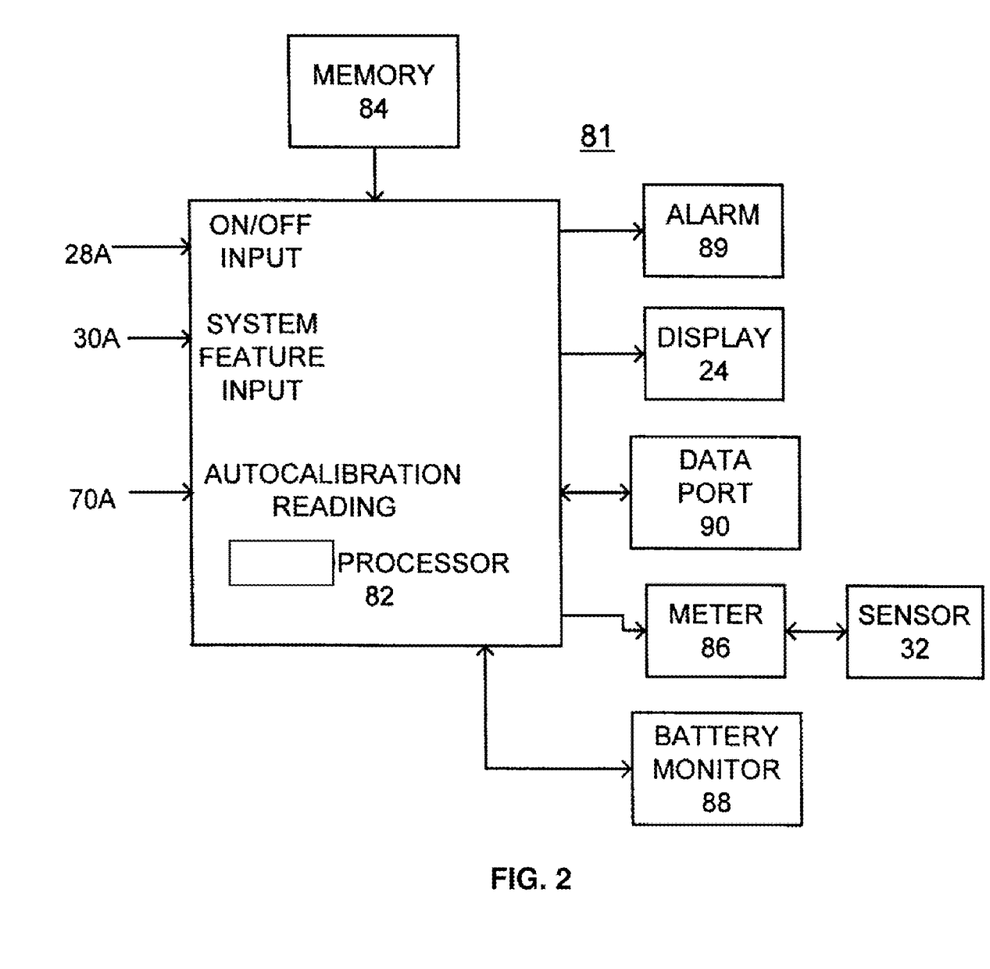
FIG. 2 illustrates a block diagram representation of sensor circuitry that may be employed according to aspects of the present invention.

FIG. 2 shows a block diagram representation of example sensor circuitry 81 for the sensor meter 10. Sensor circuitry 81 includes a processor 82 together with an associated memory 84 for storing program and user data. A meter function 86 coupled to sensor 32 is operatively controlled by the processor 82 for recording blood glucose test values. A battery monitor function 88 is coupled to the processor 82 for detecting a low battery condition. An alarm function 89 is coupled to the processor 82 for detecting predefined system conditions and for generating alarm indications for the user of sensor meter 10. A data port or communications interface 90, also shown in FIG. 1A, couples data to and from a connected computer (not shown). An ON/OFF input at a line 28A responsive to user operation of the power button 28 is coupled to the processor 82. Another input line 30A responsive to further user operation of the sensor meter 10 is coupled to the processor 82 for selectively performing system features of the sensor meter 10. An auto-calibration signal input line 70A is coupled to the processor 82 for detecting the calibration code on the auto-calibration circuit 70. The processor 82 contains suitable programming or may execute the appropriate programmed instructions from computer-readable storage media to perform operations according to aspects of the present invention.

Figure 3:
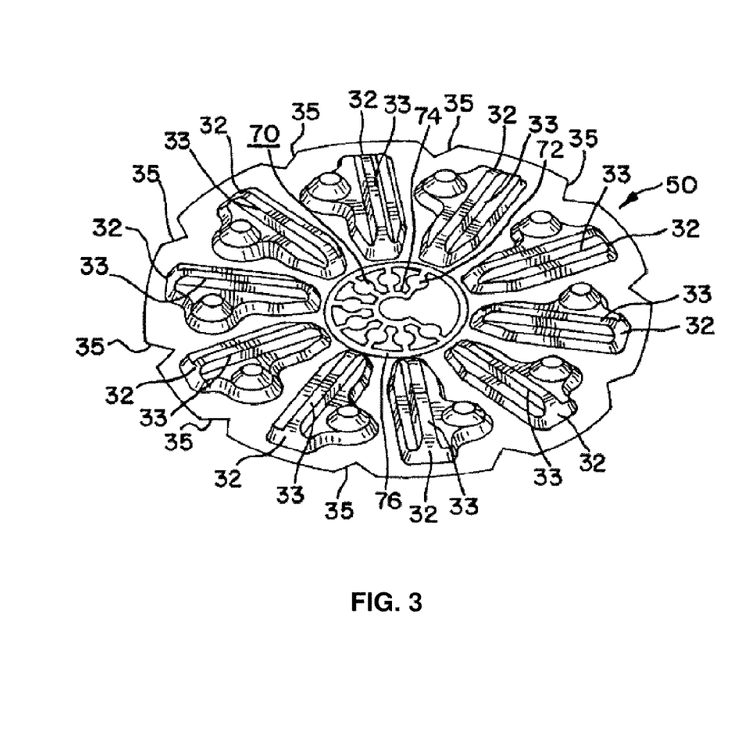
FIG. 3 illustrates an example sensor package having an auto-calibration circuit that may be employed according to aspects of the present invention.

As shown in FIG. 3, the sensor package 50 includes a plurality of test sensor cavities, or blisters, 33, each accommodating one of the plurality of test sensors 32. The sensor package 50 is generally disk-shaped with the test sensor cavities 33 extending radially from the center of the sensor package 50. The sensor package 50 also includes the auto-calibration circuit 70 providing encoded information for auto-calibration of the sensor meter 10. As discussed previously, the auto-calibration circuit 70 is used to automate the transfer of calibration information relating to the lot-specific reagent for associated sensors 32. As illustrated further in FIG. 3, the calibration information can be encoded in the circuit 70, which is disposed on a surface of the sensor package 50 containing test sensors 32 from a common origin or lot.

The auto-calibration circuit 70 includes a plurality of contact pads 72 that are arranged in predetermined positions to encode information for auto-calibration. In particular, the contact pads 72 are aligned for electrical contact with the auto-calibration pins 54 when the sensor meter 10 receives the sensor package 50. The auto-calibration circuit 70 is read, via the arrangement of contact pads 72, at any angular position and decoded by the sensor meter 10 without any user intervention. Although the auto-calibration circuit 70 may be positioned in any one of multiple, for example, ten rotary positions as the sensor package 50 is rotated during operation, the contact pads 72 are in alignment with pins 54 in the sensor meter 10 when the auto-calibration circuit 70 is read.

The auto-calibration circuit 70 may be formed by screen-printing conductive ink onto a base substrate. The substrate for the sensor package 50 may be any print receptive surface including paper, polymer-filled paper or polymer substrate, preferably a heat stabilized polyethyleneteraphthalate (PET) or polycarbonate. As such, the outer surface of the sensor package 50 in some embodiments may directly receive the conductive ink for an auto-calibration circuit 70. Alternatively, a separate substrate, e.g., a label, with an auto-calibration circuit 70 may be affixed to the sensor package 50 using an adhesive, e.g., a hot melt, UV-cure, or fast-curing adhesive. The conductive ink defining the auto-calibration circuit 70 may be a carbon, silver, or a carbon/silver blended ink.

Figure 4:
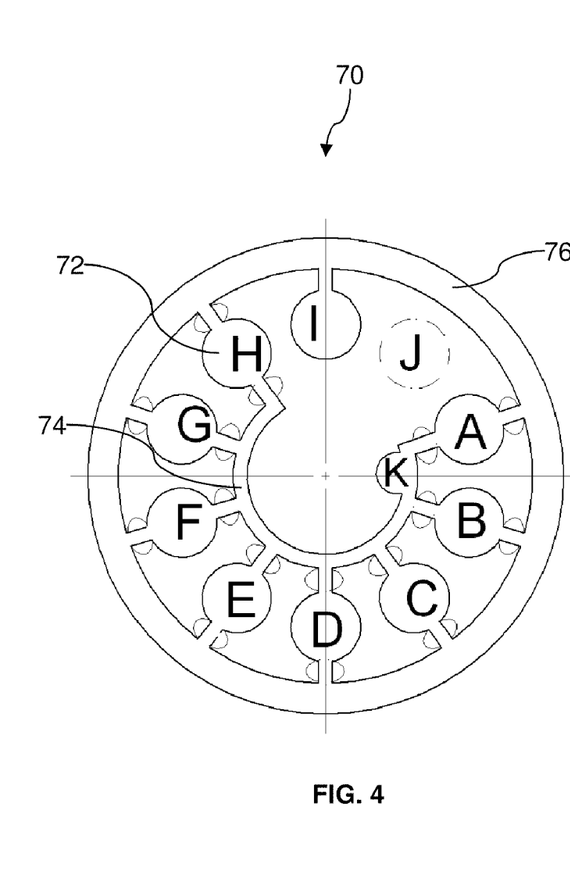
FIG. 4 illustrates an example trace pattern for an auto-calibration encoded circuit that may be employed according to aspects of the present invention.

As discussed previously, the auto-calibration circuit 70 includes a plurality of contact pads 72 that are arranged in predetermined positions to provide the encoded information for auto-calibration. The contact pads 72 are described further with reference to FIG. 4. In particular, ten contact pads 72 are represented as contact pads A through J. (The text which identifies the contacts does not actually appear on the auto-calibration circuit 70.) Traces on the auto-calibration circuit 70 define an inner ring 74 and an outer ring 76 which connect the contact pads 72 in varying relationships. Like the contact pads 72, the traces that form the inner ring 74 and the outer ring 76 are made of an electrically conductive material. Although shown as circles or partial circles, the inner ring 74 and the outer ring 76 are intended to generally represent conductive traces between the contact pads 72 and may have any shape. Calibration data is thus encoded by selectively connecting subsets of the contact pads 72 to the inner ring 74 or the outer ring 76. The connections to the inner ring 74 and the outer ring 76 may be decoded by the sensor meter 10 as corresponding binary 0's or 1's. Thus, a series of open and closed circuits representing 0 and 1 are introduced onto the auto-calibration circuit 70 to provide a calibration code. Conventional systems decode a value associated with just one of the rings 74 or 76 and use this decoded value to determine the calibrating coefficients from a lookup table embedded in the sensor meter 10. For example, the decode value for the outer ring 76 may be determined as a binary value where a connection between a contact pad 72 and the inner ring 74 may represent a binary 1 and a connection between a contact pad 72 and the outer ring 76 may represent a binary 0. In addition, contact pads 72, defined as null contacts, may be isolated from both the inner ring 74 and the outer ring 76 to increase the variety of relationships between the contact pads 72. Indeed, FIG. 4 shows that contact pad J is a designated null contact pad. As described in detail below, the arrangement of null contact pads may be employed to designate auto-calibration circuits 70 according to circuit types. In sum, selected contact pads 72 may be connected to the inner ring 74, other contacts 72 may be connected to the outer ring 76, while other contacts 72 may not be connected to either the inner ring 74 or the outer ring 76.

To minimize stock for the auto-calibration circuit 70, a single pattern advantageously may be used with subsequent punching or cutting to isolate selectively each of the ten contact pads 72, at positions A through J, from one or both of the two rings 74 or 76. For example, the contact pads 72, designated A through J, may be connected to both rings 74 or 76 in an unprogrammed circuit. A cut is made in the printed conductive material to disconnect the contact pad 72 from the inner ring 74 and/or the outer ring 76 to program the calibration code into the auto-calibration circuit 70. In one approach, a laser ablation process may be employed to cut the traces to the contact pads 72 to create unique patterns.

Figure 5:
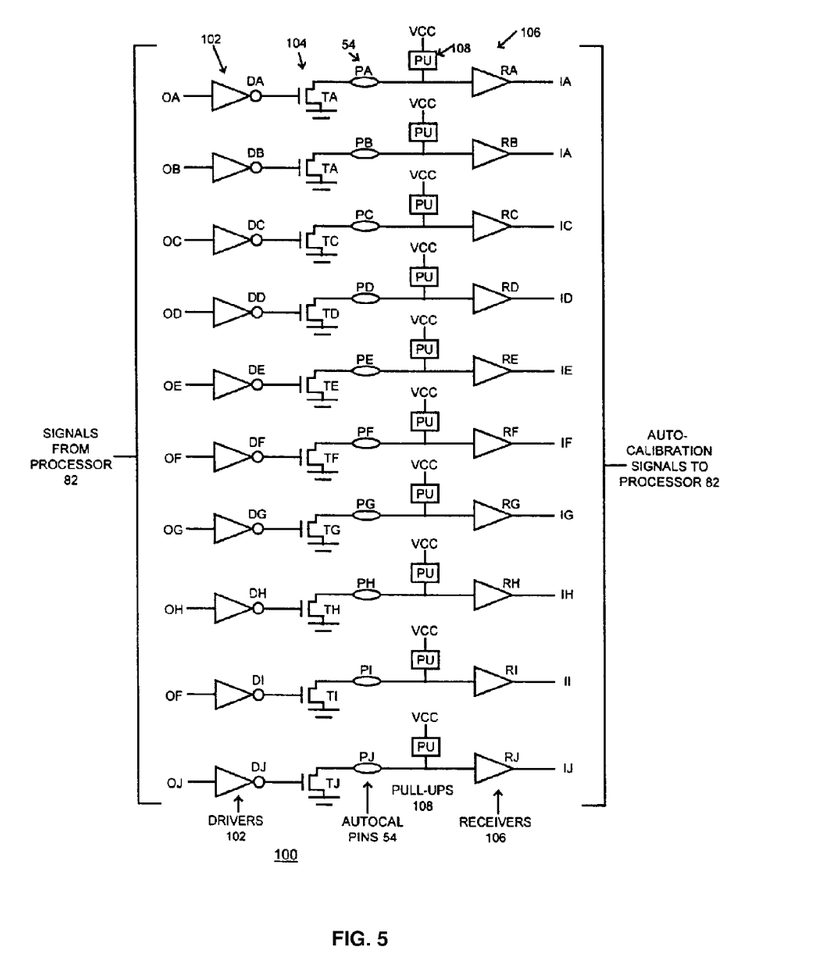
FIG. 5 illustrates an example digital electronic connection between a processor and an auto-calibration circuit according to aspects of the present invention.

FIG. 5 illustrates example digital electronic circuitry 100 for a digital calibration technique connecting the processor 82 to the auto-calibration circuit 70. Ten digital output signals from the processor 82 (OA through OJ) connect through ten drivers 102 (DA through DJ) to the ten auto-calibration pins 54 (PA through PJ) via the corresponding one of ten p-channel field-effect transistors (FETs) 104 (TA through TJ). The ten auto-calibration pins 54 connect to ten receivers 106 (RA through RJ) that provide ten digital input signals (IA through IJ) to the processor 82. Each receiver has an associated pull-up 108 (PU) connected to a supply voltage VCC. The auto-calibration pins 54 (PA through PJ) electrically connect to other contact pads 72 on the auto-calibration circuit 70 when the cover 16 is closed and an auto-calibration circuit 70 is present, due to the conductive patterns printed on the particular auto-calibration circuit 70.

In operation, to read a contact pattern of the auto-calibration circuit 70, the processor 82 turns on one of the drivers 102, while all other drivers 102 are turned off. The enabled driver 102 presents a LOW signal to the associated auto-calibration pin 54. The corresponding receiver 106 for the enabled driver 102 directly connected to the associated auto-calibration pin 54 reads as a LOW signal since this particular driver 102 and receiver 106 are directly connected. All other receivers 106 whose auto-calibration pin 54 is also driven LOW due to the low resistance connection provided by the conductive traces 74 and 76 on the circuit 70 also read as a LOW signal. The other remaining receivers 102 read as a HIGH signal since the associated driver 104 is not turned-on and the associated pull-up 108 pulls the receiver voltage to VCC. Other aspects of reading the auto-calibration circuit 70 are described in further detail below.

Referring again to FIG. 4, the contact pads 72 at positions A through J, except the isolated contact pads, are connected to only one of the inner ring 74 or the outer ring 76. To detect continuity with respect to the inner ring 74 or outer ring 76, at least two contact pads 72 are connected through the inner ring 74, and at least two contact pads 72 are connected through the outer ring 76. This arrangement also facilitates error checking because all of the contact pads 72 except for the isolated pads 72 must be accounted for in one of two continuity groups for a reading to be considered valid. For example, a missing auto-calibration circuit 70 may be detected when it appears that all contacts are isolated contacts, i.e., there are no electrical connections between meter pins 54 because the continuity provided by the auto-calibration circuit 70 is missing. As shown in FIG. 4, one contact pad, i.e., contact pad I, is always connected to the outer ring 76 according to example rules for encoding the auto-calibration circuit 70. It is noted that although FIG. 4 shows a particular configuration for the auto-calibration circuit 70 and certain rules are described with respect to this configuration, other configurations are also operable according to aspects of the present invention. For example, other embodiments may employ a different number of contact pads and may apply different rules for positioning the contact pads.

FIG. 4 also illustrates a contact pad K, which may be used in the manufacturing process to apply a test voltage to the auto-calibration circuit 70 prior to shipment. In particular, the contact pad K is connected to the inner ring 74. Thus, a testing procedure may apply a 10 V DC signal between the contact pad K and the contact pad I, which is connected to the outer ring 76. The procedure reads the 1/0 bit pattern for the other contact pads, and the voltage is then reversed to read the 0/1 bit pattern. Although the contact pad K is illustrated in FIG. 4, it is not necessary to practice aspects of the present invention. The presence of the contact pad K, however, facilitates mechanical alignment of a test head for a testing procedure and provides a visual indicator for alignment of the pins 54 over the contact pads 72 for testing.

The arrangement of null contact pads may be employed to designate auto-calibration circuits 70 according to circuit types. The different types of auto-calibration circuits may indicate different sensor types, for example, corresponding to different product models, etc. When an auto-calibration label is employed, the type may be conventionally referred to as "a label type." In some systems, designating auto-calibration circuits 70 according to types may require two contact pads to remain electrically isolated from all other contact pads. The arrangement of the two null contact pads indicates the type. For example, FIG. 4 shows that contact pad J is always isolated, so one other contact pad must be isolated to provide the two null contact pads. According to the example rules illustrated in FIG. 4, the contact pad always connected to the outer ring 76, i.e., contact pad I, is disposed one position counter-clockwise from the designated isolated contact pad, i.e., contact pad J. Meanwhile, the remaining seven contact pads 72 are connected to at least one other contact pad 72 through the inner ring 74 or the outer ring 76.

As discussed previously, to minimize stock for the auto-calibration circuit, a single pattern may be used with subsequent punching, cutting, or forming to isolate selectively each of the ten contact pads 72, at positions A through J, from one or both of the two rings 74 or 76. However, in the example of FIG. 4, contact pad I is always connected to the outer ring 76 and contact pad J is always an isolated contact pad. As a result, only contact pads A through H in this case need to be connected to both the inner ring 74 and the outer ring 76 in the unprogrammed stock. Moreover, because the contact pad J is always isolated, the contact pad J does not have to be physically produced on the stock, for example, with the application of conductive ink. The contact pad J, or any designated isolated contact pad, just needs to correspond to a designated area or position on the auto-calibration circuit 70 that is electrically isolated from the two rings 74 and 76 and the other contact pads 72.

To indicate a circuit type for the auto-calibration circuit 70, conventional systems employ the number of contact pads between the two isolated contact pads as an indicator. For example, referring to FIG. 4, contact J and one other isolated contact pad may be adjacent to each other or separated by one, two, or three other contact pads connected to the rings 74 and 76. Isolated contact pads that are adjacent to each other may correspond with a "type 1" circuit. Isolated contact pads separated by one other contact pad may correspond to a "type 2" circuit. Isolated contact pads separated by two other contact pads may correspond to a "type 3" circuit. Isolated contact pads separated by three other contact pads may correspond to a "type 4" circuit. For example, as shown in TABLE 1, a conventional system may identify circuit types 1, 2, 3 and 4 by detecting a separation of zero contact pads between isolated contact pads J and A, a separation of one contact pad between isolated contact pads J and B, a separation of two contact pads between isolated contact pads J and C, and a separation of three contact pads between isolated contact pads J and D, respectively.

TABLE 1

| Circuit Type | No. of Connected Contacts Between Isolated Contacts | Arrangement of Isolated Contact Pads |
| --- | --- | --- |
| 1 | 0 | Isolated contact pads J and A |
| 2 | 1 | Isolated contact pads J and B separated by connected contact pad A |
| 3 | 2 | Isolated contact pads J and C separated by connected contact pads A and B |
| 4 | 3 | Isolated contact pads J and D separated by connected contact pads A, B, and C |

An approach for decoding the auto-calibration circuit 70 involves performing four read steps. In the first step, all pins are connected as inputs and one pin is selected as an output and driven LOW. A first read is performed, and the corresponding pattern returns all contact pads that are connected to the driven pin as LOWs. In other words, any contact pads 72 that are on the same ring 74 or 76 as the driven contact pad also registers LOW due to the electrical connection via the common ring 74 or 76. The contacts that are not connected to the driven pin register HIGH. In the second step, the HIGH-LOW pattern is decoded to find the first HIGH pin from the first read. The first HIGH pin is driven LOW and a second read is performed. In the third step, the second HIGH-LOW pattern is decoded to find the next HIGH pin from both of the first two reads. This next HIGH pin is then driven LOW and a third read is performed. In the fourth step, the third HIGH-LOW pattern is decoded to find the next HIGH pin from the first three reads. The pin is then driven LOW and a fourth read is performed. These four read steps enable the sensor meter 10 to determine the positions of the isolated contact pads and the patterns for the contact pads connected to the inner ring 74 and the outer ring 76. Each of the readings is required to determine each set of contact pads 72: the set connected to the inner ring 74, the set connected to the outer ring 76, one isolated contact pad, and the other isolated contact pad. Because the isolated contact pads are not connected to either ring 74 or 76, they register LOW when either ring 74 or 76 is set LOW. Thus, as discussed previously, there must be at least two contact pads connected to each ring to make it possible to determine which contact pads are isolated. In conventional systems, once the isolated contact pads are identified, the separation between the isolated contact pads may be determined to obtain the circuit type.

Although the separation between the isolated contacts may indicate the circuit type, a separation of one, two, and three connected contact pads can each be achieved according to two different configurations with respect to contact pad J. In particular, a separation of one connected contact pad can be achieved when the isolated contact pads include contact pad J and contact pad B, or when the isolated contact pads include contact pad J and contact pad H. In addition, a separation of two connected contact pads can be achieved when the isolated contact pads include contact pad J and contact pad C, or when the isolated contact pads include contact pad J and contact pad G. Furthermore, a separation of three connected contact pads can be achieved when the isolated contact pads include contact pad J and contact pad D, or when the isolated contact pads include contact pad J and contact pad F. Accordingly, conventional systems that determine the number of contact pads separating the isolated contact pads to identify the circuit type cannot differentiate between an auto-calibration circuit 70 having isolated contact pads J and B or isolated contact pads J and H. Similarly, an auto-calibration circuit 70 having isolated contact pads J and C or isolated contact pads J and G would be indistinguishable. Meanwhile, an auto-calibration circuit 70 having isolated contact pads J and D or isolated contact pads J and F would be indistinguishable. As a result, in conventional systems, the contact pads F, G, H are not used as isolated contact pads when the contact pads B, C, and D are used as isolated contact pads, or vice versa, because isolated contact pad pairs J and F, J and G, and J and H are not uniquely distinguishable from isolated contact pad pairs J and D, J and C, and J and B, respectively. Although not described in the current example, it is noted that contact pad E may also be isolated with contact pad J.

When contact pad J and one of contact pads A, B, C, and D are isolated and contact pad I is connected to the outer ring 76, the remaining seven contact pads are connected to the inner ring 74 or the outer ring 76. For example, if contact pads J and B are isolated for a type 2 circuit, the remaining seven contact pads would be contact pads A and C through H. The seven remaining contact pads represent $2^7=128$ possible combinations of connections. However, the combination where none of the remaining contact pads is connected to the inner ring 74 must be excluded, because at least two contact pads must be connected to the inner ring 74. Correspondingly, the seven combinations where only one of the remaining contact pads is connected to the inner ring 74 must also be excluded. In addition, the combination where all remaining contact pads are connected to the inner ring 74 must be excluded, because contact pad I and at least one of the remaining contact pads must be connected to the outer ring 76. Thus, for each pair of isolated contact pads (J and A, J and B, J and C, J and D), the corresponding circuit type 1, 2, 3, or 4 provides 119 unique combinations for the calibration code. In total, circuit types 1, 2, 3, and 4 provide 476 unique combinations. However, in some cases, the rules for encoding the auto-calibration circuit 70 may exclude other combinations. For example, combinations which decode to certain values, such as 0, 1, 2, 4, 8, 16, etc, may be considered invalid.

The number of unique combinations in conventional systems is limited, because, as described previously, relying on the separation of isolated contact pads to determine circuit type precludes some contact pads from being isolated. Embodiments according to aspects of the present invention, however, are not limited in this manner and provide an extended read/decode functionality that increases the number of unique combinations over the number allowed by such conventional systems. In particular, these embodiments employ the binary nature of the auto-calibration circuit 70 to allow more isolated contact pads to be uniquely detectable and more circuit types to be decoded. For instance, in the example of FIG. 4, aspects of the present invention allow one of contact pads B, C, D, E, F, G, and H to be isolated with contact pad J. Unlike an approach that determines the circuit type according to the number of contact pads separating the isolated contact pads, the isolated contact pad pairs J and F, J and G, and J and H are uniquely distinguishable from isolated contact pad pairs J and D, J and C, and J and B, respectively. Using the four-step read technique and allowing contact pads F, G, and H to be isolated with contact pad J provides an additional 357 unique combinations for calibration codes. If contact pad E is also isolated in combination with contact pad J, an additional 476 unique codes are provide, doubling the number of unique codes from the previous example to 952.

Referring to TABLE 2, the binary nature of the auto-calibration circuit 70 of FIG. 4 is shown. In particular, TABLE 2 shows a decode value corresponding to each possible isolated contact when the auto-calibration circuit 70 is read by the four-step read technique discussed previously. Contact pad A corresponds with the least significant bit (LSB) and contact pad J corresponds with the most significant bit (MSB). For example, an isolated space at contact pad A decodes as 111111110 (decimal value of 1022); an isolated space at contact pad B decodes as 1111111101 (decimal value of 1021); and so on. The decode values shown in TABLE 2 represent a binary offset to a base value of 1023. In other words, decode value of isolated contact pad A=1023−1=1022; decode value of isolated contact pad B=1023−2=1021; decode value of isolated contact pad C=1023−4=1019; decode value of isolated contact pad D=1023−8=1015; decode value of isolated contact pad E=1023−16=1007; decode value of isolated contact pad F=1023−32=991; decode value of isolated contact pad G=1023−64=959; decode value of isolated contact pad H=1023−128=895; decode value of isolated contact pad I=1023−256=767; and decode value of isolated contact pad J=1023−512=511.

Using the four-step read technique described previously, an auto-calibration circuit with two isolated contact pads according to the present invention returns a value of 511 for the J contact pad and an additional value indicated in TABLE 2 corresponding to the other isolated contact pad. For example, when contact pads J and B are isolated, the four-step read technique returns a value of 511 for isolated contact pad J and a value of 1021 for isolated contact pad B. In general, the values decoded for the auto-calibration circuit 70 includes two values for the isolated contact pads. As TABLE 2 shows, each isolated contact pad is associated with a uniquely identifiable number. Accordingly, embodiments according to aspects of the present invention can use the two values to identify the isolated contact pads and the circuit type indicated by the particular pair of isolated contact pads.

It is noted that embodiments according to aspects of the present invention may require the auto-calibration circuit 70 to be loaded into the sensor meter 10 in the same, known orientation each time so that the contact pads 72 can be initially identified as contact pads A, B, C, etc. and the auto-calibration circuit 70 can be correctly read and decoded. For example, proper orientation of the sensor package 50 in the sensor meter 10 ensures that the pins 54 designated to read each contact pad are not positioned over incorrect contact pads resulting in improper decoding of the auto-calibration circuit 70. Once the contact pads 72 are identified, the sensor package 50 may rotate as required within to dispense the test sensors 32. For example, to ensure that the user loads the sensor package 50 according to the proper initial orientation, a colored arrow or some other marking may be imprinted on the sensor package 50 to provide the user with a visual indicator. Alternatively, the locking projections 65 and their corresponding recessed portions 35 as shown in FIG. 1B may be spaced unequally about the indexing disk 64 and the sensor package 50, respectively, so that the recessed portions 35 can engage the locking projections 65 if the sensor package 50 is inserted into the sensor meter 10 according to a specific orientation.

TABLE 2

| Isolated Contact Pad | Binary Code | Decimal Code |
|---|---|---|
| A | 1111111110 | 1022 |
| B | 1111111101 | 1021 |
| C | 1111111011 | 1019 |
| D | 1111110111 | 1015 |
| E | 1111101111 | 1007 |
| F | 1111011111 | 991 |
| G | 1110111111 | 959 |
| H | 1101111111 | 895 |
| I | 1011111111 | 767 |
| J | 0111111111 | 511 |

The designated isolated contact pad J decodes as 511 for all circuit types and may be used if any rotation of the sensor package 50 within the sensor meter 10 must be determined. The decode process indicates an illegal "zero" value when all values shown in TABLE 2 are returned, i.e., 1022 for contact pad A, 1021 for contact pad B, and so on. An auto-calibration circuit cannot provide a zero value, and thus a zero value indicates that no auto-calibration circuit is present.

As shown in TABLE 3, the four-step read technique also provides example decode values corresponding to the inner ring 74 and the outer ring 76 of the auto-calibration circuit 70. In particular, the example decode values are provided for each of the eight circuit types 1-8 indicated by isolated contact pad pairs J and A; J and B; J and C; J and D; J and E; J and F; J and F; J and G; and J and H, respectively. For the binary decode value corresponding to the inner ring 74, each connection between a contact pad 72 and the outer ring 76 corresponds to a binary 0. For the binary decode value corresponding to the outer ring 76, each connection between a contact pad 72 and the inner ring 74 corresponds to a binary 0. It is noted that the isolated contact pads are represented as binary 1's in binary decode values for both the inner ring 74 and the outer ring 76. As discussed previously, the contact pad A corresponds with the least significant bit (LSB) and contact pad J corresponds with the most significant bit (MSB).

Referring to TABLE 4, it can be shown that the sum of the inner ring decode value and the outer ring decode value for a given auto-calibration circuit and circuit type always sums to the same value. For example, all auto-calibration circuits within a circuit type 2 having isolated contact pads J and B each have an inner ring decode value and an outer ring decode value that sum to 1537. As shown in TABLE 3, a type 2 circuit with contact pads D, E, F, G, H, and I connected to the outer ring 76 has an inner ring decode value of 519 and an outer ring decode value of 1018, which sum to 1537. Similarly, a type 2 circuit with contact pads C, E, F, G, H, and I connected to the outer ring 76 has an inner ring decode value of 523 and an outer ring decode value of 1014, which sum to 1537. Thus, the sum of the inner decode value and the outer ring decode value provides an additional indicator of the circuit type.

Furthermore, the sum of the inner ring decode value and the outer ring decode value for the circuit types can be expressed as binary offsets to a value of 1535. In other words, sum of decode values for type 1 circuit=1535+1=1536; sum of decode values for type 2 circuit=1535+2=1537; sum of decode values for type 3 circuit=1535+4=1539; sum of decode values for type 4 circuit=1535+8=1543; sum of decode values for type 5 circuit=1535+16=1551; sum of decode values for type 6 circuit=1535+32=1567; sum of decode values for type 7 circuit=1535+64=1599; and sum of decode values for type 8 circuit=1535+128=1663.

TABLE 3

| Isolated Contact Pads | Contact Pads Connected to Outer Ring | Binary Decode Value for Inner Ring | Decimal Decode Value for Inner Ring | Binary Decode Value for Outer Ring | Decimal Decode Value for Outer Ring |
|---|---|---|---|---|---|
| J, A (Type 1) | C, E, F, G, H, I | 1000001011 | 523 | 1111110101 | 1013 |
| J, A (Type 1) | B, E, F, G, H, I | 1000001101 | 525 | 1111110011 | 1011 |
| J, A (Type 1) | E, F, G, H, I | 1000001111 | 527 | 1111110001 | 1009 |
| ... | ... | ... | ... | ... | ... |
| J, B (Type 2) | D, E, F, G, H, I | 1000000111 | 519 | 1111111010 | 1018 |
| J, B (Type 2) | C, E, F, G, H, I | 1000001011 | 523 | 1111110110 | 1014 |
| J, B (Type 2) | A, E, F, G, H, I | 1000001110 | 526 | 1111110011 | 1011 |
| ... | ... | ... | ... | ... | ... |
| J, C (Type 3) | D, E, F, G, H, I | 1000000111 | 519 | 1111111100 | 1020 |
| J, C (Type 3) | B, E, F, G, H, I | 1000001101 | 525 | 1111110110 | 1014 |
| J, C (Type 3) | A, E, F, G, H, I | 1000001110 | 526 | 1111110101 | 1013 |
| ... | ... | ... | ... | ... | ... |
| J, D (Type 4) | C, E, F, G, H, I | 1000001011 | 523 | 1111111100 | 1020 |
| J, D (Type 4) | B, E, F, G, H, I | 1000001101 | 525 | 1111111010 | 1018 |
| J, D (Type 4) | A, E, F, G, H, I | 1000001110 | 526 | 1111111001 | 1017 |
| ... | ... | ... | ... | ... | ... |
| J, E (Type 5) | C, D, F, G, H, I | 1000010011 | 531 | 1111111100 | 1020 |
| J, E (Type 5) | B, D, F, G, H, I | 1000010101 | 533 | 1111111010 | 1018 |
| J, E (Type 5) | A, D, F, G, H, I | 1000010110 | 534 | 1111111001 | 1017 |
| ... | ... | ... | ... | ... | ... |
| J, F (Type 6) | C, D, E, G, H, I | 1000100011 | 547 | 1111111100 | 1020 |
| J, F (Type 6) | B, D, E, G, H, I | 1000100101 | 549 | 1111111010 | 1018 |
| J, F (Type 6) | A, D, E, G, H, I | 1000100110 | 550 | 1111111001 | 1017 |
| ... | ... | ... | ... | ... | ... |
| J, G (Type 7) | C, D, E, F, H, I | 1001000011 | 579 | 1111111100 | 1020 |
| J, G (Type 7) | B, D, E, F, H, I | 1001000101 | 581 | 1111111010 | 1018 |
| J, G (Type 7) | A, D, E, F, H, I | 1001000110 | 582 | 1111111001 | 1017 |
| ... | ... | ... | ... | ... | ... |
| J, H (Type 8) | C, D, E, F, G, I | 1010000011 | 643 | 1111111100 | 1020 |
| J, H (Type 8) | B, D, E, F, G, I | 1010000101 | 645 | 1111111010 | 1018 |
| J, H (Type 8) | A, D, E, F, G, I | 1010000110 | 646 | 1111111001 | 1017 |
| ... | ... | ... | ... | ... | ... |

TABLE 4

| Isolated Contact Pads | Sum of Inner and Outer Ring Decode Values |
|---|---|
| J, A (Type 1) | 1536 |
| J, B (Type 2) | 1537 |
| J, C (Type 3) | 1539 |
| J, D (Type 4) | 1543 |
| J, E (Type 5) | 1551 |
| J, F (Type 6) | 1567 |
| J, G (Type 7) | 1599 |
| J, H (Type 8) | 1663 |

Accordingly, rather than determining the circuit type of an auto-calibration circuit 70 according to the separation between isolated contact pads, embodiments according to aspects of the present invention determine the circuit type from the decode values associated with the isolated contact pads. In addition, embodiments can confirm the circuit type by determining the sum of the decode value associated with the inner ring 74 and the decode value associated with the outer ring 76. Advantageously, the auto-calibration circuit 70 used by conventional systems can be used by embodiments of the present invention. In particular, a new manufacturing process is not required to produce an auto-calibration circuit that is operable according to aspects of the present invention.

Figure 6:
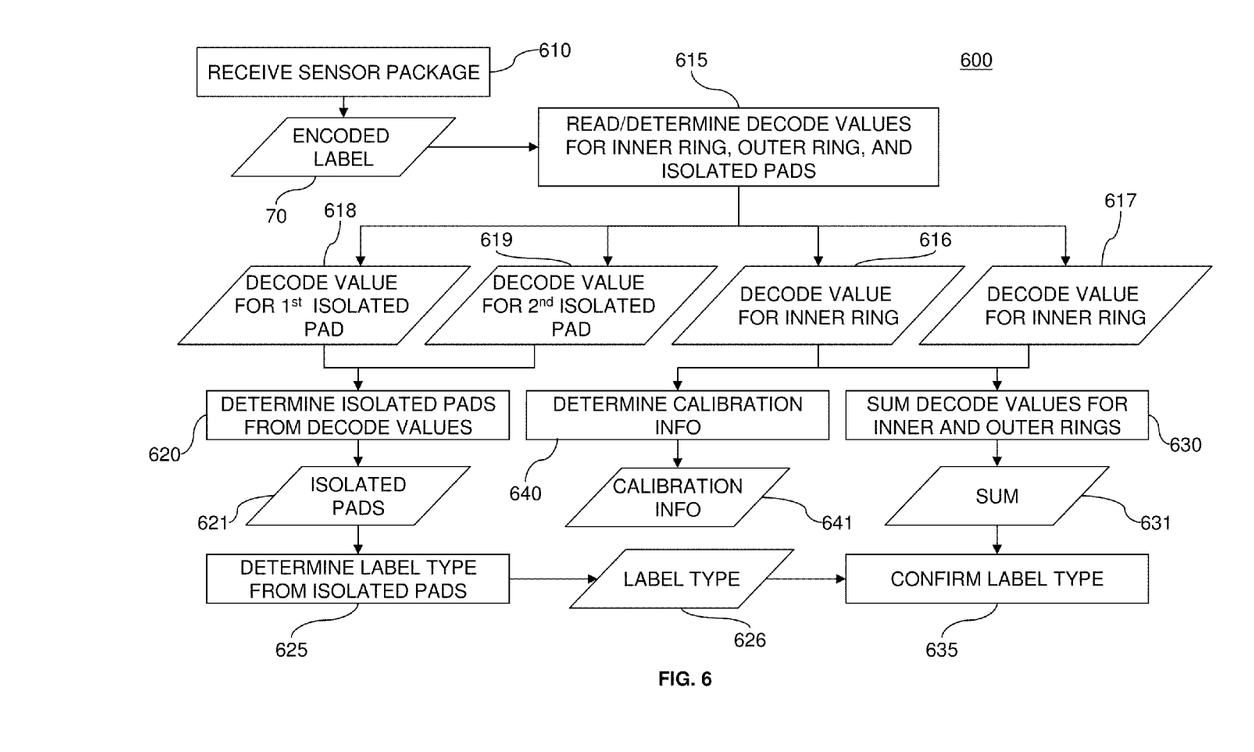
FIG. 6 illustrates an example decode process to determine a type for an auto-calibration circuit and calibration information according to aspects of the present invention.

For example, as illustrated by the example approach 600 FIG. 6, in act 610, the sensor package 50 having the auto-calibration circuit 70 is received, e.g., by the sensor meter 10. In act 615, the auto-calibration circuit 70 is read to determine the decode value 616 corresponding to the inner ring 74, the decode value 617 outer ring 76, the decode value 618 corresponding to the first isolated contact pad, and the decode value 619 corresponding to the second isolated contact pad.

In act 620, the isolated contact pads 621 are identified from the decode values 618 and 619, and in act 625, the circuit type 626 is determined from the identified isolated contact pads 621. In act 630, a sum 631 of the decode values 616 and 617 is determined, and in act 635, this sum 631, which corresponds uniquely with one of the circuit types, is used to confirm the circuit type 626 identified in act 625. In act 640, one of the decode values 616 and 617 is translated into calibration information 641, e.g., via a lookup table, to adjust the operation of the sensor meter 10. Act 640 may be enhanced by determining the calibration information 641 separately from the decode value 616 of the inner ring 74 and the decode value 617 of the outer ring 76, as the calibration information should be the same for both decode values 616 and 617.

Embodiments according to aspects of the present invention also support auto-calibration circuits with three isolated contact pads, e.g., isolated contact pads J, A, and B, which provide an additional 28 subgroups of 56 unique combinations for a total of 1,568 unique combinations. To identify the three isolated contact pads, the conventional read technique described previously requires one additional read step. According to one approach, the four read steps are executed as previously described. If an additional HIGH bit remains after the four read steps, an additional read is required to decode the auto-calibration circuit 70. Otherwise, if this additional HIGH bit does not remain, the auto-calibration circuit 70 only has two isolated contact pads and can be decoded by the four read steps.

The unique decode values shown, for example, in TABLE 2, are the same for auto-calibration circuits having two or three isolated contact pads. For example, if contact pads J, A, and B on the auto-calibration circuit 70 are isolated, the read steps would return a values of 511 for contact pad J, 1022 for contact pad A, and 1021 for contact pad B.

TABLE 5 shows provides example decode values corresponding to the inner ring 74 and the outer ring 76 of an auto-calibration circuit 70 having three isolated contact pads. In particular, the example decode values are provided for circuit types indicated by isolated contact pad combinations J, A, and B; J, A, and C; J, A and D; J, A, and E; J, B, and C; J, B, and D; J, B, and E; and J, B, and F.

Referring to TABLE 6, it can be shown that the sum of the inner ring decode value and the outer ring decode value for a given auto-calibration circuit and circuit type always sums to the same value. To provide an example, TABLE 6 shows the sums corresponding to auto-calibration circuits 70 that have isolated contact pads J, A, and B; J, A, and C; J, A, and D; J, A, and E; J, A, and F; J, A, and F; J, A, and G; J, A, and H; J, B, and C; J, B, and D; J, B, and E; J, B, and F; J, B, and G; and J, B, and H. For instance, all auto-calibration circuits 70 having isolated contact pads J, A, and B each have an inner ring decode value and an outer ring decode value that sum to 1538. As shown in TABLE 5, an auto-calibration circuit 70 with isolated contact pads J, A, and B in combination with contact pads E, F, G, H, and I connected to the outer ring 76 has an inner ring decode value of 527 and an outer ring decode value of 1011, which sum to 1538. Similarly, an auto-calibration circuit 70 with isolated contact pads J, B, and C in combination with contact pads E, F, G, H, and I connected to the outer ring 76 has an inner ring decode value of 527 and an outer ring decode value of 1014, which sum to 1541.

Furthermore, the sum of the inner ring decode value and the outer ring decode value for the circuit types can be expressed as binary offsets to a value, e.g., 1536 for auto-calibration circuits having isolated contact pads J, A, and one of contact pads B through H. For example, the sum of decode values where contact pads J, A, and B are isolated=1536+2=1538; the sum of decode values where contact pads J, A, and C are isolated=1536+4=1540; the sum of decode values where contact pads J, A, and D are isolated=1536+8=1544; the sum of decode values where contact pads J, A, and E are isolated=1536+16=1552; the sum of decode values where contact pads J, A, and F are isolated=1536+32=1568; the sum of decode values where contact pads J, A, and G are isolated=1536+64=1600; and the sum of decode values where contact pads J, A, and H are isolated=1535+128=1664.

TABLE 5

| Isolated Contact Pads | Contact Pads Connected to Outer Ring | Binary Decode Value for Inner Ring | Decimal Decode Value for Inner Ring | Binary Decode Value for Outer Ring | Decimal Decode Value for Outer Ring |
|---|---|---|---|---|---|
| J, A, B | E, F, G, H, I | 1000001111 | 527 | 1111110011 | 1011 |
| J, A, B | D, F, G, H, I | 1000010111 | 535 | 1111101011 | 1003 |
| J, A, B | C, F, G, H, I | 1000011011 | 539 | 1111100111 | 999 |
| ... | ... | ... | ... | ... | ... |
| J, A, C | E, F, G, H, I | 1000001111 | 527 | 1111110101 | 1013 |
| J, A, C | D, F, G, H, I | 1000010111 | 535 | 1111101101 | 1005 |
| J, A, C | B, F, G, H, I | 1000011101 | 541 | 1111100111 | 999 |
| ... | ... | ... | ... | ... | ... |
| J, A, D | E, F, G, H, I | 1000001111 | 527 | 1111111001 | 1017 |
| J, A, D | C, F, G, H, I | 1000011011 | 539 | 1111101101 | 1005 |
| J, A, D | B, F, G, H, I | 1000011101 | 541 | 1111101011 | 1003 |
| ... | ... | ... | ... | ... | ... |
| J, A, E | D, F, G, H, I | 1000010111 | 535 | 1111111001 | 1017 |
| J, A, E | C, F, G, H, I | 1000011011 | 539 | 1111110101 | 1013 |
| J, A, E | B, F, G, H, I | 1000011101 | 541 | 1111110011 | 1011 |
| ... | ... | ... | ... | ... | ... |
| J, B, C | E, F, G, H, I | 1000001111 | 527 | 1111110110 | 1014 |
| J, B, C | D, F, G, H, I | 1000010111 | 535 | 1111101110 | 1006 |
| J, B, C | A, F, G, H, I | 1000011110 | 542 | 1111100111 | 999 |
| ... | ... | ... | ... | ... | ... |
| J, B, D | E, F, G, H, I | 1000001111 | 527 | 1111111010 | 1018 |
| J, B, D | C, F, G, H, I | 1000011011 | 539 | 1111101110 | 1006 |
| J, B, D | A, F, G, H, I | 1000011110 | 542 | 1111101011 | 1003 |
| ... | ... | ... | ... | ... | ... |
| J, B, E | D, F, G, H, I | 1000010111 | 535 | 1111111010 | 1018 |
| J, B, E | C, F, G, H, I | 1000011011 | 539 | 1111110110 | 1014 |
| J, B, E | A, F, G, H, I | 1000011110 | 542 | 1111110011 | 1011 |
| ... | ... | ... | ... | ... | ... |
| J, B, F | D, E, G, H, I | 1000100111 | 551 | 1111111010 | 1018 |
| J, B, F | C, E, G, H, I | 1000101011 | 555 | 1111110110 | 1014 |
| J, B, F | A, E, G, H, I | 1000101110 | 558 | 1111110011 | 1011 |
| ... | ... | ... | ... | ... | ... |

TABLE 6

| Isolated Contact Pads | Sum of Inner and Outer Ring Decode Values |
|---|---|
| J, A, B | 1538 |
| J, A, C | 1540 |
| J, A, D | 1544 |
| J, A, E | 1552 |
| J, A, F | 1568 |
| J, A, G | 1600 |
| J, A, H | 1664 |
| J, B, C | 1541 |
| J, B, D | 1545 |
| J, B, E | 1553 |
| J, B, F | 1569 |
| J, B, G | 1601 |
| J, B, H | 1665 |

Further embodiments may employ four isolated contact pads which provide an additional 336 subgroups of 25 unique combinations for a total 8,736 unique combinations. Such embodiments may require modification of the four-step read technique described previously. Accordingly, embodiments of the present invention may provide more than unique combinations for circuit designs that have heretofore been limited to 476 unique combinations.

In view of the foregoing, the embodiments advantageously expand the usability of the auto-calibration circuit by providing new subgroups, i.e., circuit types, that can be assigned to future meter products without further changes in the design of the auto-calibration circuit or the technique for reading the auto-calibration circuit.

While the present invention has been described in connection with a number of exemplary embodiments, and implementations, the present inventions are not so limited, but rather cover various modifications, and equivalent arrangements.

What is claimed is:

1. A system for determining a characteristic of a test sample, comprising:
   a sensor meter responsive to a test sensor, the sensor meter determining a characteristic of the test sample received on the test sensor; and
   a calibration element including electrical contacts readable by the sensor meter, the electrical contacts being configurable in one of a plurality of patterns that communicates, to the sensor meter, information relating to the determination of the characteristic of the test sample, the plurality of patterns including two or more of the electrical contacts being electrically isolated from any other electrical contacts, wherein each of the isolated electrical contacts is associated with a unique value and the sensor meter determines at least partially the information from the electrical contacts by determining a combination of the unique values associated with the isolated electrical contacts.

2. The system of claim 1, wherein the test sensor includes a reagent that reacts with the test sample, the sensor meter determines the characteristic of the test sample by measuring the reaction between the reagent and the test sample, and the measurement by the sensor meter is calibrated by the information from the calibration element.

3. The system of claim 2, wherein the information from the calibration element relates to a source for the reagent on the test sensor, and the information calibrates the sensor meter to account for the source.

4. The system of claim 1, wherein the plurality of patterns for the electrical contacts represents binary values, and the sensor meter determines at least partially the information from the electrical contacts by determining a combination of binary values associated with the isolated electrical contacts.

5. The system of claim 1, wherein the plurality of patterns are organized into types, and the combination of the unique values associated with the isolated electrical contacts indicates one of the types.

6. The system of claim 5, wherein the sensor meter is one of a plurality of sensor meter types, the plurality of patterns are operable with the plurality of sensor meter types and are organized into the sensor meter types, and the combination of the unique values associated with the isolated electrical contacts indicates a type corresponding to the sensor meter.

7. The system of claim 1, wherein the sensor meter determines the information from the calibration element and translates the information into coefficients for an equation that determines the characteristic of the test sample.

8. The system of claim 1, wherein the plurality of patterns for the electrical contacts includes at least one subset of the electrical contacts being electrically connected to each other, and the sensor meter further determines the information from the electrical contacts by determining a value corresponding to the at least one subset of connected electrical contacts.

9. The system of claim 8, wherein the plurality of patterns for the electrical contacts includes a first subset of the electrical contacts connected to each other via a first conductive path and a second subset of the electrical contacts connected to each other via a second conductive path.

10. The system of claim 9, wherein the sum of the value corresponding to the first subset of connected electrical contacts and the value corresponding to the second subset of connected electrical contacts uniquely corresponds to the combination of the unique values associated with the isolated electrical contacts.

11. The system of claim 1, further comprising a sensor package receivable by the sensor meter, the sensor package containing the test sensor and including the calibration element.

12. The system of claim 1, wherein the test sample is a fluid sample and the characteristic is a concentration of an analyte in the fluid sample.

13. A method for determining a characteristic of a test sample, comprising:
reading a calibration element, the calibration element including electrical contacts configurable in one of a plurality of patterns to communicate information relating to a determination of a characteristic of a test sample, the plurality of patterns including two or more of the electrical contacts being electrically isolated from other electrical contacts, each of the isolated electrical contacts being associated with a unique value;
determining at least partially the information from the electrical contacts by determining a combination of the unique values associated with the isolated electrical contacts; and
determining a characteristic of a test sample according to the information from the calibration element.

14. The method of claim 13, wherein determining a characteristic of the test sample comprises measuring, with a sensor meter, a reaction between the test sample and a reagent, the measurement being calibrated by the information from the calibration element.

15. The method of claim 14, wherein the information from the calibration element relates to a source for the reagent, and the information calibrates the sensor meter to account for the source.

16. The method of claim 13, wherein the plurality of patterns for the electrical contacts represents binary values, and determining the information from the electrical contacts comprises determining a combination of binary values associated with the isolated electrical contacts.

17. The method of claim 13, wherein the plurality of patterns are organized into types, and the combination of the unique values associated with the isolated electrical contacts indicates one of the types.

18. The method of claim 17, wherein the calibration element is operable with a plurality of sensor meter types, and the combination of the unique values associated with the isolated electrical contacts indicate a type corresponding to one of the sensor meter types.

19. The method of claim 13, further comprising translating the information into coefficients for an equation, wherein determining a characteristic of the test sample comprises solving the equation with the coefficients.

20. The method of claim 13, further comprising determining the information from the electrical contacts by determining a value corresponding to at least one subset of the electrical contacts that are electrically connected to each other.

21. The method of claim 20, wherein the plurality of patterns for the electrical contacts includes a first subset of the electrical contacts connected to each other via a first conductive path and a second subset of the electrical contacts connected to each other via a second conductive path.

22. The method of claim 21, wherein the sum of the value corresponding to the first subset of connected electrical contacts and the value corresponding to the second subset of connected electrical contacts uniquely corresponds to the combination of the unique values associated with the isolated electrical contacts.

23. The method of claim 22, further comprising confirming, with the sum, the combination of the unique values associated with the isolated electrical contacts.

24. The method of claim 13, wherein the calibration element is included in a sensor package, the sensor package containing a test sensor that receives the test sample.

25. The method of claim 13, wherein the test sample is a fluid sample and the characteristic is a concentration of an analyte in the fluid sample.

26. A system for providing a calibration circuit with a type indicator, the calibration circuit providing information relating to a determination of a characteristic of a test sample, comprising:

an electrical circuit; and a calibration circuit including electrical contacts readable by the electrical circuit, the electrical contacts being configurable in one of a plurality of patterns that communicates, to the electrical circuit, information relating to a determination of a characteristic of a test sample, the plurality of patterns including two or more of the electrical contacts being electrically isolated from any other electrical contacts, each of the isolated electrical contacts being associated with a unique value, the electrical circuit determining at least partially the information from the electrical contacts by determining a combination of the unique values associated with the isolated electrical contacts, wherein the plurality of patterns are organized into types, and the combination of the unique values associated with the isolated electrical contacts indicates one of the types for the calibration circuit.

27. The system of claim 26, wherein the information from the calibration circuit relates to a source for a reagent that reacts with the test sample to determine the characteristic of the test sample, and the information calibrates a measurement of the test sample according to the source.

28. The system of claim 26, wherein the plurality of patterns for the electrical contacts represents binary values, and the electrical circuit determines at least partially the information from the electrical contacts by determining a combination of binary values associated with the isolated electrical contacts.

29. The system of claim 26, wherein the electrical circuit determines the information from the calibration circuit and translates the information into coefficients for an equation that determines the characteristic of the test sample.

30. The system of claim 26, wherein the plurality of patterns for the electrical contacts includes at least one subset of the electrical contacts being electrically connected to each other, and the electrical circuit further determines the information from the electrical contacts by determining a value corresponding to the at least one subset of connected electrical contacts.

31. The system of claim 30, wherein the plurality of patterns for the electrical contacts includes a first subset of the electrical contacts connected to each other via a first conductive path and a second subset of the electrical contacts connected to each other via a second conductive path.

32. The system of claim 31, wherein the sum of the value corresponding to the first subset of connected electrical contacts and the value corresponding to the second subset of connected electrical contacts uniquely corresponds to the combination of the unique values associated with the isolated electrical contacts.

* * * * *